US012677854B2

(12) United States Patent
     Häkämies

(10) Patent No.:  US 12,677,854 B2
(45) Date of Patent:        Jul. 14, 2026

(54) EGG REPLACEMENT FOOD PRODUCT AND METHOD OF PRODUCING THEREOF COMPRISING MICROBIAL PROTEIN BIOMASS

(71) Applicant: Solar Foods Oyj, Vantaa (FI)

(72) Inventor: Anna Häkämies, Lappeenranta (FI)

(73) Assignee: Solar Foods Oyj, Vantaa (FI)

( * ) Notice: Subject to any disclaimer, the term of this patent is extended or adjusted under 35 U.S.C. 154(b) by 277 days.

(21) Appl. No.: 18/552,223

(22) PCT Filed: Apr. 7, 2022

(86) PCT No.: PCT/FI2022/050227
     § 371 (c)(1),
     (2) Date: Sep. 25, 2023

(87) PCT Pub. No.: WO2022/229502
     PCT Pub. Date: Nov. 3, 2022

(65) Prior Publication Data
     US 2024/0156138 A1        May 16, 2024

(30) Foreign Application Priority Data
     Apr. 27, 2021    (FI) ..................................... 20215485

(51) Int. Cl.
     *A23L 15/00*          (2016.01)
     *A23D 9/00*           (2006.01)
     (Continued)

(52) U.S. Cl.
     CPC ................ *A23L 15/35* (2016.08); *A23D 9/00* (2013.01); *A23J 1/008* (2013.01); *A23J 3/20* (2013.01);
     (Continued)

(58) Field of Classification Search
     CPC ............. A23J 3/225; A23J 1/008; A23J 15/35
     (Continued)

(56)              References Cited

U.S. PATENT DOCUMENTS 4,103,038 A  *  7/1978  Roberts .................... A23J 3/08
                                                          426/601
     10,070,654 B2    9/2018  Keys et al.
                                  (Continued)

FOREIGN PATENT DOCUMENTS

CN        111436576 A    7/2020
     RU        2660274 C1     7/2018
                    (Continued)

OTHER PUBLICATIONS

Liu Yanfeng et al: "Food synthetic biology-driven protein supply transition: From animal-derived production to microbial fermentation", Chinese Journal of Chemical Engineering, vol. 30, Dec. 8, 2020 (Dec. 8, 2020), pp. 29-36, XP55940223, CN, ISSN: 1004-9541, DOI: 10.1016/j.cjche.2020.11.014, 4 pages.
                    (Continued)

*Primary Examiner* — Jennifer McNeil
(74) *Attorney, Agent, or Firm* — Espatent Oy

(57)              ABSTRACT

Disclosed is a method of producing an egg replacement food product that includes mixing a protein microbial biomass powder with water to obtain a wet mixture, hydrating the wet mixture at room temperature, mixing the wet mixture at high speed, hydrating the mixed wet mixture at 6 C degrees, mixing the hydrated wet mixture with an oil at high speed and emulsifying the mixed wet mixture, homogenizing the emulsified mixed wet mixture, heating the homogenized wet mixture up to from 85 C up to 90 C degrees, and adding sodium chloride (NaCl) and citric acid to the heated wet mixture and mixing to obtain pH from 3.5 up to 4.0.

13 Claims, 1 Drawing Sheet

(51) Int. Cl.

| | |
|---|---|
| *A23J 1/00* | (2006.01) |
| *A23J 3/20* | (2006.01) |
| *A23J 3/22* | (2006.01) |
| *A23L 29/00* | (2016.01) |
| *C12N 1/20* | (2006.01) |

(52) U.S. Cl.
CPC ............. *A23J 3/225* (2013.01); *A23L 29/015* (2016.08); *A23L 29/03* (2016.08); *C12N 1/20* (2013.01)

(58) Field of Classification Search
USPC .................................................. 426/656, 657
See application file for complete search history.

(56) References Cited

U.S. PATENT DOCUMENTS

| | | | |
|---|---|---|---|
| 10,321,705 | B2 | 6/2019 | Bansal-Mutalik et al. |
| 2004/0166230 | A1 | 8/2004 | Bodor et al. |
| 2010/0297325 | A1 | 11/2010 | Brooks et al. |
| 2020/0138066 | A1 | 5/2020 | Anchel |

FOREIGN PATENT DOCUMENTS

| | | | | | |
|---|---|---|---|---|---|
| WO | 8605362 | A2 | 9/1986 | | |
| WO | 2017014806 | A1 | 1/2017 | | |
| WO | 2020261245 | A1 | 12/2020 | | |
| WO | 2021022082 | A1 | 2/2021 | | |
| WO | 2021071895 | A1 | 4/2021 | | |
| WO | WO-2021116949 | A1 * | 6/2021 | ............... | C12N 1/12 |

OTHER PUBLICATIONS

Yang Xiaoyong et al: "Microbial protein production from CO2, H2, and recycled nitrogen: Focusing on ammonia toxicity and nitrogen sources", Journal of Cleaner Production, Elsevier, Amsterdam, NL, vol. 291, Jan. 11, 2021 (Jan. 11, 2021), XP086500532, ISSN: 0959-6526, DOI: 10.1016/J.JCLEPRO.2021.125921, 5 pages.

European Patent Office, International Search Report and Written Opinion, Application No. PCT/FI2022/050227, mailed Jul. 21, 2022, 21 pages.

Finnish Patent and Registration Office, Search Report, Application No. 20215485, mailed Sep. 28, 2021, 2 pages.

\* cited by examiner

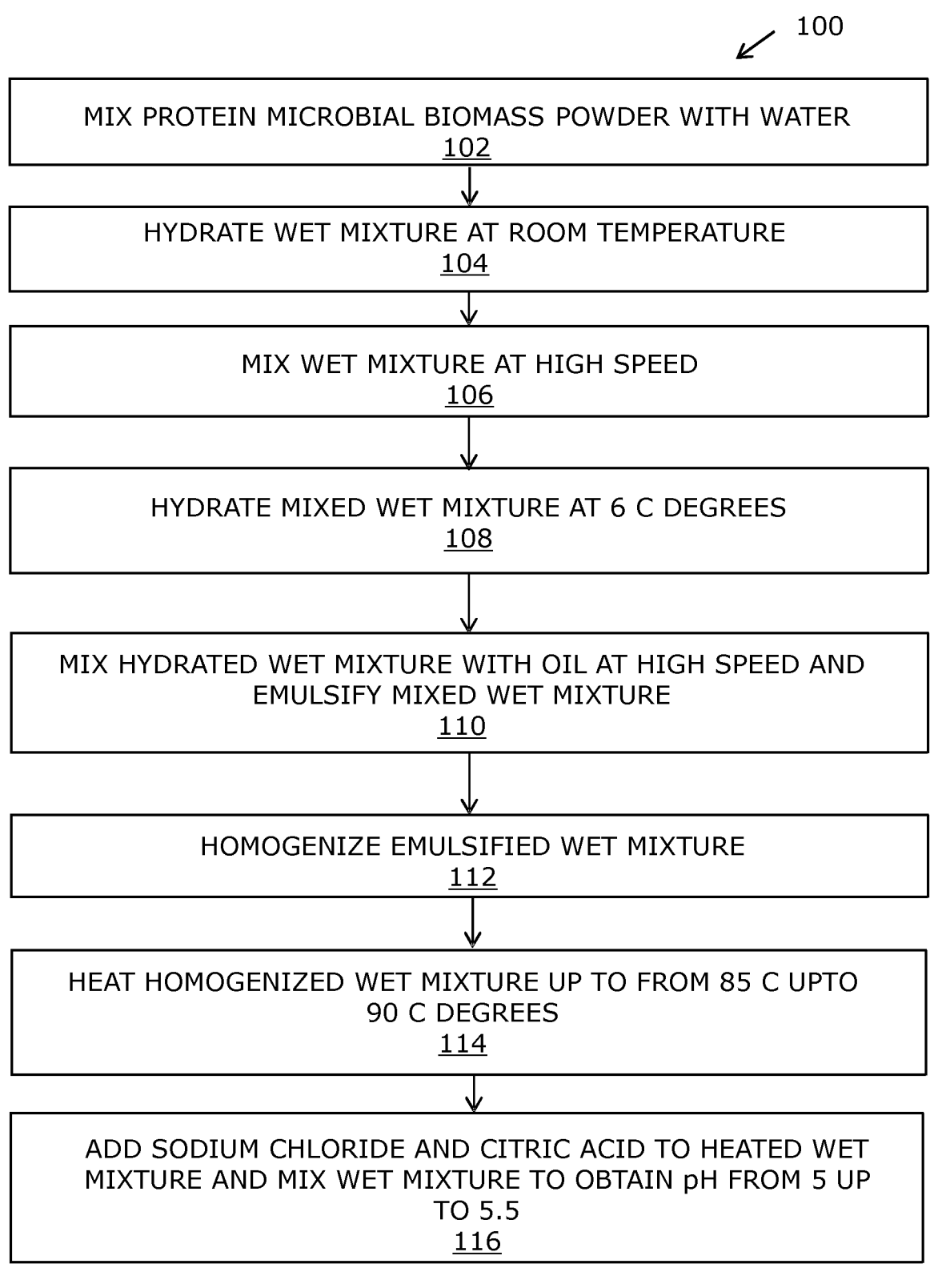

100

MIX PROTEIN MICROBIAL BIOMASS POWDER WITH WATER
102

HYDRATE WET MIXTURE AT ROOM TEMPERATURE
104

MIX WET MIXTURE AT HIGH SPEED
106

HYDRATE MIXED WET MIXTURE AT 6 C DEGREES
108

MIX HYDRATED WET MIXTURE WITH OIL AT HIGH SPEED AND EMULSIFY MIXED WET MIXTURE
110

HOMOGENIZE EMULSIFIED WET MIXTURE
112

HEAT HOMOGENIZED WET MIXTURE UP TO FROM 85 C UPTO 90 C DEGREES
114

ADD SODIUM CHLORIDE AND CITRIC ACID TO HEATED WET MIXTURE AND MIX WET MIXTURE TO OBTAIN pH FROM 5 UP TO 5.5
116

EGG REPLACEMENT FOOD PRODUCT AND METHOD OF PRODUCING THEREOF COMPRISING MICROBIAL PROTEIN BIOMASS

TECHNICAL FIELD

The present disclosure relates generally to alternatives for animal-based meat products; and more specifically, to egg replacement food products.

BACKGROUND

In recent times, there has been a boom of health-conscious consumers, who are in search of nutritious, wholesome and sustaining food products with minimum detrimental impact on their physical health. Traditionally, the human diet consists of meat (such as for example cattle, poultry, pig, fish) and plants (such as for example legumes, rice) to meet the required proteins, carbohydrates, fats, vitamins and minerals in proper proportions. Moreover, the biggest challenge in the availability of meat is the growing population, as increased meat production affects the environment. Consequently, in the present century, one has gained the ability to make a clone of natural things, one of them being, successful reproduction of traditional food products using plant-based products. Subsequently, this leads to appealing a wider segment of consumers who do not consume meat and its products like vegetarians, vegans and some non-vegetarians seeking to reduce their meat consumption. Therefore, the global food industry is required to adapt to comparatively more sustainable and healthier alternatives for animal-based meat products (such as for example, eggs).

Particularly, eggs are multipurpose and nearly omnipresent food which provide a high nutritional content. However, eggs have many disadvantages. For example, the fat and cholesterol found in eggs may harm heart health and lead to prostate cancer. Furthermore, the consumption of too much protein from the egg whites are linked with kidney disease, kidney stones and the likes. Typical alternatives to eggs are egg-like plant-based products produced from plants such as soybeans, corns, peanuts and so forth. Furthermore, these egg-like plant-based products may have higher fiber, lower saturated fat content, and antioxidants. However, these egg-like plant-based structures are not very known, as these are quite difficult to reproduce. Furthermore, the egg-like plant-based products have a typical bean-off flavor that makes it difficult to flavor to imitate the egg-like flavor. Also, the egg-like plant-based products are poor in other nutrients, such as for example iron, vitamin D, vitamin B 12, choline and antioxidants like lutein and zeaxanthin. These nutrients play an important role in bone halth, cognition, energy, pregnancy and eye health.

Current advances in development of alternatives of meat and its products make use of microbial cells such as yeast, algae and so forth. In this regard, techniques such as cell culture followed by homogenization, and so forth have been employed to produce egg-like plant-based products. Moreover, the egg-like plant-based products, lack the egg-like texture and other characteristics, and are not suitable for consumption by mammals, such as humans and animals, mostly due to the poor digestibility. Normally, when such an egg-like plant-based products is ingested, the epithelial cells of bowels act as a physical barrier with the production of a mucus layer that prevents the endotoxins from translocating into the bloodstream. However, in case of endotoxernia or leaky gut syndrome, endotoxins translocate to bloodstreams due to mucosal degradation, and result in health risks ranging from allergies to fatal toxic reactions.

Therefore, in light of the foregoing discussion, there exists a need to overcome drawbacks associated with conventional techniques of producing the egg-like plant-based products that has egg-like texture and improved digestibility.

SUMMARY

The present disclosure seeks to provide a method of producing an egg replacement food product. The present disclosure also seeks to provide a composition of the egg replacement food product. An aim of the present disclosure is to provide a solution that overcomes at least partially the problems encountered in prior art.

In one aspect, the present disclosure provides a method of producing an egg replacement food product, the method comprising:

mixing a protein microbial biomass powder with water to obtain a wet mixture;

hydrating the wet mixture at room temperature;

mixing the wet mixture at high speed;

hydrating the mixed wet mixture at 6 C degrees;

mixing the hydrated wet mixture with an oil at high speed and emulsifying the mixed wet mixture;

homogenizing the emulsified mixed wet mixture;

heating the homogenized wet mixture up to from 85 C up to 90 C degrees;

adding sodium chloride (NaCl) and citric acid to the heated wet mixture and mixing to obtain pH from 3.5 up to 4.0.

In another aspect, the present disclosure provides an egg replacement food product comprising from 76% up to 78% of water;

from 9% up to 10% of the protein microbial biomass powder;

from 0.7% up to 1.1% of sodium chloride (NaCl);

from 9% up to 10% of the oil.

Embodiments of the present disclosure substantially eliminate or at least partially address the aforementioned problems in the prior art, and enable efficient method of producing egg replacement food product in a manner that it comprises all the vitamins, minerals and antioxidants, and has a more egg-like texture with no bean-off flavour Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein:

FIG. 1 illustrates a flowchart depicting steps of a method of producing an egg replacement food product, in accordance with an embodiment of the present disclosure.

In the accompanying drawing, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides a method of producing an egg replacement food product, the method comprising:

mixing a protein microbial biomass powder with water to obtain a wet mixture;

hydrating the wet mixture at room temperature;

mixing the wet mixture at high speed;

hydrating the mixed wet mixture at 6 C degrees;

mixing the hydrated wet mixture with an oil at high speed and emulsifying the mixed wet mixture;

homogenizing the emulsified mixed wet mixture;

heating the homogenized wet mixture up to from 85 C up to 90 C degrees;

adding sodium chloride (NaCl) and citric acid to the heated wet mixture and mixing to obtain pH from 3.5 up to 4.0.

In another aspect, an embodiment of the present disclosure provides an egg replacement food product comprising from 76% up to 78% of water;

from 9% up to 10% of the protein microbial biomass powder;

from 0.7% up to 1.1% of sodium chloride (NaCl);

from 9% up to 10% of the oil.

The present disclosure provides the aforementioned method of producing an egg replacement food product and the egg replacement food product. The method of the present disclosure comprises utilising protein microbial biomass powder derived from microbial biomass of microorganisms, mixed with liquid, salt and spices, and producing egg replacement food product. Beneficially, the method is efficient and less labour-intensive. Furthermore, the egg replacement food product using the aforesaid method is animal-free, vegan and plant-based alternative to eggs that are made with turmeric and mung bean protein to create egg-like texture and flavour, and therefore, is suitable for vegetarian and vegan consumers. Additionally, beneficially, the meat analogue food ingredient is readily digestible by humans and animals and supplies them with high-quality protein, iron and vitamins such as B12. For the sake of brevity, hereinafter the term "egg replacement food product" is used interchangeably with the term "final product".

Throughout the present disclosure, the term "protein microbial biomass powder" as used herein refers to a nutritional supplement, extracted from microbes of bacteria, yeast, fungi, and algae for example, in dehydrated form. Herein the term "biomass" refers to a measure of amount of living component (namely, bacteria) in a sample. Generally, the protein microbial biomass powder provides a concentrated source of proteins with no or negligible carbohydrates, fats or any other compounds. Alternatively, the protein microbial biomass powder comprises proteins and could be fortified with compounds such as vitamins and minerals, such as calcium, iron, and so forth. It will be appreciated that proteins are essential for muscle building and recovery. Therefore, protein consumption should be monitored to supply the required amount of proteins in the diet, while avoiding long-term excessive protein intake that affects kidneys, liver and body's bone-and-calcium balance.

The method comprises mixing a protein microbial biomass powder with water to obtain a wet mixture. Optionally, the protein microbial biomass powder comprises isolated bacterial strain deposited as VTT-E-193585 or a derivative thereof. Strain VTT-E-193585 (SoF1) has been deposited on Jun. 11, 2019 in the VTT Culture Collection at the VTT Technical Research Centre of Finland, P.O. Box 1000, FI-02044 VTT, Finland, an International Depositary Authority under the Budapest Treaty. The said isolated bacterial strain or a derivative thereof is typically a gram-negative bacterium (which do not retain crystal violet stain used in the gram-staining method). It will be appreciated that the said isolated bacterial strain or a derivative thereof is genetically stable and can be grown in a broad range of process conditions, ranging from optimal to stressful conditions, over time. Beneficially, the said strain or the derivative thereof comprises iron and vitamin B12. Moreover, a final product resulting from the said strain or the derivative thereof does not a bean-off-flavour and is therefore easier to flavour. Possibly, the final product also has umami (namely, savoury or "meat-like") flavour.

Optionally, the protein microbial biomass powder is produced via upstream and downstream processes. The term "downstream process" as used herein refers to the process that follows the selection of microbial cells, such as for example bacterial cells, making high yield of protein. Typically, the downstream process comprises unit operations that facilitate production of the final product in a manner useful for the consumers (humans or animals) thereof. In this regard, the downstream processing comprises subjecting the bacterial cells to physiological, chemical and mechanical conditions, to provide a final product that is suitable and safe for use by the consumers.

In an embodiment, firstly, the bacterial cells in the downstream process are cultivated by gas fermentation to obtain microbial biomass. Herein, bioreactor cultivation is the main unit where, the bacterial cells loaded into the bioreactor from a stock solution are cultivated in controlled conditions. In particular, the feedstock necessary for cell growth, for instance carbon dioxide ($CO_2$), hydrogen ($H_2$), oxygen ($O_2$), ammonia ($NH_3$), minerals and so forth are fed into the bioreactor. Furthermore, the cell growth in the bioreactor is continuous and the bacterial cell microbial biomass leaves the bioreactor when target cell density is reached. Moreover, the bacterial cells after reaching the target cell density are incubated, wherein the incubating is selected to be at least one of a batch incubation and/or continuous incubation to obtain necessary cell density in microbial biomass. Secondly, a liquid phase (growth medium) and a solid phase of the microbial biomass are separated and the microbial biomass is concentrated by removing the liquid phase. At this stage, the microbial biomass is 10 times concentrated by removal of the liquid phase comprising about 5% of dry matter in comparison to the earlier 0.7% dry matter. Finally, the microbial biomass is dried to obtain a protein microbial biomass powder. Typically, drum drying is used to obtain the protein microbial biomass powder. Herein, drum drying is used for drying out the liquid phase at relatively low temperatures over rotating, high-capacity drums that produce sheets of the drum-dried product.

Optionally, the downstream process further comprises incubating the microbial biomass with a heat treatment at temperature from 55 C up to 75 C degrees from 15 minutes up to 40 minutes. The incubation may for example be carried out at temperatures 55, 56, 57, 58, 59, 60, 65 or 70 C degrees up to 56, 57, 58, 59, 60, 65, 70 or 75 C degrees for the incubation period from 15, 20, 25, 30 or 35 minutes up to 20, 25, 30, 35 or 40 minutes. Notably, the incubation at 60, 61, 62 or 65 C degrees up to 61, 62, 65 or 68 C degrees has an impact on hydrolysis of cell wall structures leading to partial removal of lipopolysaccharadies-containing components (or "endotoxins") during seperation. Beneficially, the microbial cell wall (or "cell wall") hydrolysis results in a final product with 10-1000 times lower endotoxin response. Additionally, incubation at the aforesaid temperature range prevents growth of unwanted microbial cells and kills bacterial cells and result in a pure culture of only the desired bacterial cells.

Optionally, the downstream process further comprises homogenizing the bacterial cells of the microbial biomass before drying step. The term "homogenizing" as used herein refers to a means of physical disruption of the bacterial cell walls. Herein, homogenizing could be carried out using a high-pressure homogenization (HPH), wherein physical or mechanical process of forcing a stream of sample, such as the concentrated microbial biomass, through a high-pressure homogenizing device to homogenize the bacterial cells and/or reduce the particle size of any components. Typically, homogenization is carried out at 900 bars.

Typically, homogenizing at least partially degrades cell walls of the bacterial cell. Furthermore, homogenizing makes the final product more meat like. Beneficially, if the cell wall is broken, digestion becomes easier. Additionally, protein can be obtained with high-pressure homogenization or possibly milling. Furthermore, the homogenizing is carried out at pressure ranging from 800, 900, 1000, 1200 or 1500 bars up to 900, 1000, 1200, 1500 or 2000 bars. Herein, the final product is improved by reducing the endotoxins levels. Furthermore, milling degrades bacterial cells and releases proteins.

Optionally, a feed for cultivating by gas fermentation comprises at least one of selected from $CO_2$, methane ($CH_4$), $H_2$, $O_2$, $NH_3$, or at least one mineral. Herein, minerals containing ammonium, phosphate, potassium, sodium, vanadium, iron, sulphate, magnesium, calcium, molybdenum, manganese, boron, zinc, cobalt, selenium, iodine, copper and/or nickel are added.

In an embodiment, the microbial biomass pH is adjusted from 7.4, 7.5 or 7.6 up to 7.5, 7.6 or 8.0 after separating the liquid phase. It will be appreciated that a suitable pH is an essential factor for the growth media to facilitate bacterial growth. Herein, pH is adjusted before or after homogenization. In case pH of protein microbial biomass powder is under 7.0, a meat-like texture with extrusion is not obtained.

The method comprises hydrating the wet mixture at room temperature. Herein, the protein microbial biomass powder is soaked in water by letting it be in the container with water. Furthermore, the protein microbial biomass powder absorbs the water. Herein, at least some hydration time ranging from 90 or 100 minutes up to 100 or 110 minutes is necessary.

The method comprises mixing the wet mixture at high speed. Herein, high-speed mixing, preferably in range of 1000-28000 rotations per minute (rpm) for a minute is necessary before homogenizing, as the protein microbial biomass powder is very dry. The high-speed mixing may for example be carried out at from 1000, 1100, 1500, 2000, 5000, 10000 or 20000 rotations per minute (rpm) up to 1500, 2000, 5000, 10000, 20000 or 28000 rotations per minute (rpm). Furthermore, high-speed mixing is necessary for obtaining even dispersion. Notably, industrial scale high speed or shear mixers, for instance Silverson, IKA Ultra Turrax and so forth are used to obtain even dispersion.

The method comprises hydrating the mixed wet mixture at 6 C degrees. Herein, the mixed wet mixture is hydrated until fully hydrated. Optionally, the mixed wet mixture is left for overnight for at least 16 hours for the protein microbial biomass powder to absorb water.

The method comprises mixing the hydrated wet mixture with an oil at high speed and emulsifying the mixed wet mixture. Herein, the oil is any neutral tasting oils. Furthermore, the oil is selected to be at least one of a rapeseed oil, a sunflower oil or a soy oil, because of their neutral taste.

Beneficially, the oil is added to obtain an emulsion that will enable formation of the final product. Henceforth, the addition of emulsifier is not necessary, as the protein microbial biomass powder already comprises emulsifier. Furthermore, the oil improves gelling effect that take place in a final heating. Typically, the high-speed mixing may be performed at 20000 rotations per minute (rpm) for 2 minutes using the IKA Ultra Turrax homogenizer. Finally, In the final heating, the emulsion is heated to form a structure called "emulsion-gel". Notably, a real egg contains 10% fat, hence the oil is used to imitate the nutritional value of the real egg. Additionally, oil can enhance mouthfeel by making the final product smoother.

The method comprises homogenizing the emulsified mixed wet mixture. Herein, the homogenizing is carried out at from 500 bars up to 1200 bars. The homogenizing may for example be carried out at from 500, 600, 700, 800, 900 or 1000 bars up to or 500, 600, 700, 800, 900, 1000 or 1200 bars. In an example, the emulsified mixed wet mixture may be homogenized at 500 bars for 2 runs or at 800 bars for 1 run. Furthermore, in case a batch machine is used, the mixed wet mixture is mixed at least twice, carried out at at least 800 bars. Notably, when the pressure is lower than 500 bars, the structure of the emulsified wet mixture obtained is not good. Herein, high pressure homogenizer such as SPX FLOW homogenizer, is used for pressure higher than 500 bars.

The method comprises heating the homogenized wet mixture up to from 85 C up to 90 C degrees. The homogenized wet mixture, for example, may be heated from 85, 86 or 87 C degrees up to 86, 87 or 90 C degrees. Herein, bacteria is removed by pasteurizing or sterilizing. Furthermore, a stabilized homogenized structure is obtained by heating. Notably, heating is important for final texture formation. Furthermore, if common salt (NaCl) is added before heating, scrambled egg like structure is obtained with heating. In case the homogenized wet mixture is not heated, the scrambled egg like structure is not obtained in the final heating step. Herein, the heating opens protein structure that helps citric acid to precipitate proteins. Subsequently, precipitation take place because citric acid lowers the pH and proteins are closer to their isoelectric point where they are not water soluble anymore.

The method comprises adding sodium chloride (NaCl) and citric acid to the heated wet mixture and mixing to obtain pH from 3.5 up to 4.0. The pH, for example may be from 3.5, 3.6, 3.7, 3.8 or 3.9 up to 3.6, 3.7, 3.8, 3.9 or 4.0. Herein, heat may be provided to the wet mixture by means of a frying pan. Notably, heating is a necessary step, wherein NaCl and citric acid are added after heating from 85, 86, 87, 88 or 89° C. up to 86, 87, 88, 89 or 90° C. Furthermore, heating in a frying pan will take place if the final product is liquid egg-like stuff in the bottle and consumer makes scrambled egg at home. In case the final product is ready-to-eat scrambled egg, then heating may be provided by industrial ovens, microwaves, stoves or other heating systems.

Optionally, the mixed wet mixture with a pH from 3.5 up to 4.0 comprises:

from 76% up to 78% of water;

from 9% up to 10% of the protein microbial biomass powder;

from 0.7% up to 1.1% of sodium chloride (NaCl);

from 9% up to 10% of the oil.

Optionally, in this regard, the mixed wet mixture with a pH from 3.5, 3.6, 3.7, 3.8 or 3.9 up to 3.6, 3.7, 3.8, 3.9 or 4.0 comprises water which may for example be 76 or 77% up to 77 or 78% of the total amount of mixed wet mixture. Furthermore, the amount of sodium chloride (NaCl) may for example be from 0.7, 0.8, 0.9 or 1.0% up to 0.8, 0.9, 1.0 or 1.1%. The mixed wet mixture with aforementioned parameters resulted in a better egg resembling structure with no remarkable side taste.

Furthermore, if sodium chloride and citric acid are added after heating, the mixed wet mixture needs to be heated again for obtaining the scrambled egg like structure. However, if sodium chloride and citric acid are added before heating, additional heating is not necessary. It will be appreciated that citric acid aids in precipitation. Furthermore, sodium chloride may also aid in precipitation.

The present disclosure also relates to the egg replacement food product as described above. Various embodiments and variants disclosed above apply mutatis mutandis to the egg replacement food product.

Optionally, the oil is selected to be at least one of a rapeseed oil, a sunflower oil, a soy oil. Using oils having neutral taste enables to give better taste and mouth feeling of an egg replacement food product.

Optionally, the protein microbial biomass powder comprises isolated bacterial strain deposited as VTT-E-193585 or a derivative thereof.

Optionally, the egg replacement food product is obtained by the aforementioned method.

DETAILED DESCRIPTION OF THE DRAWINGS

Referring to FIG. 1, there is shown a flowchart 100 illustrating steps of a method of producing an egg replacement food product, in accordance with an embodiment of the present disclosure. At step 102, protein microbial biomass powder is mixed with water. At step 104, the wet mixture is hydrated at room temperature. At step 106, the wet mixture is mixed at high speed. At step 108, the mixed wet mixture is hydrated at 6 C degrees. At step 110, the hydrated wet mixture is mixed with an oil at high speed and the mixed wet mixture is emulsified. At step 112, the emulsified wet mixture is homogenized. At step 114, the homogenized wet mixture is heated up to from 85 up to 90 C degrees. At step 116, NaCl and citric acid are added to the heated wet mixture and mix the wet mixture to obtain pH from 3.5 up to 4.0.

The steps 102, 104, 106, 108, 110, 112, 114 and 116 are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A method of producing an egg replacement food product, the method comprising:

mixing a protein microbial biomass powder, comprising isolated bacterial strain deposited as VTT-E-193585 or a derivative thereof with water to obtain a wet mixture;

hydrating the wet mixture at room temperature;

mixing the wet mixture at high speed;

hydrating the mixed wet mixture at 6 C degrees;

mixing the hydrated wet mixture with an oil at high speed and emulsifying the mixed wet mixture;

homogenizing the emulsified mixed wet mixture;

heating the homogenized wet mixture up to from 85 C up to 90 C degrees;

adding sodium chloride (NaCl) and citric acid to the heated wet mixture and mixing to obtain pH from 3.5 up to 4.0.

2. The method according to claim 1 further comprising heating the mixed wet mixture having pH from 3.5 up to 4.0.

3. The method according to claim 1, wherein total weight of the wet mixture with a pH from 3.5 up to 4.0 comprises:

from 76% up to 78% of water;

from 9% up to 10% of the protein microbial biomass powder comprising isolated bacterial strain deposited as VTT-E-193585 or a derivative thereof;

from 0.7% up to 1.1% of sodium chloride (NaCl);

from 9% up to 10% of the oil.

4. The method according to claim 1, wherein the oil is selected to be at least one of a rapeseed oil, a sunflower oil, a soy oil.

5. The method according to claim 1, wherein homogenizing is carried out at from 500 bars up to 1200 bars.

6. The method according to claim 1, wherein the protein microbial biomass powder is produced via upstream and downstream processes, the downstream process comprising following steps:

cultivating bacterial cells by gas fermentation to obtain a microbial biomass;

separating a liquid phase and a solid phase of the microbial biomass and concentrating the microbial biomass by removing the liquid phase;

drying the microbial biomass to obtain the protein microbial biomass powder.

7. The method according to claim 6, wherein the downstream process further comprises incubating the microbial biomass with a heat treatment at temperature from 55 C up to 75 C degrees from 15 minutes up to 40 minutes.

8. The method according to claim 6, wherein the downstream process further comprises homogenizing the bacterial cells of the microbial biomass before drying step.

9. The method according to claim 8, wherein the homogenizing is carried out at pressure from 800 bars up to 2000 bars for at least one run.

10. The method according to claim 6, wherein a feed for cultivating by gas fermentation comprises at least one of selected from CO2, CH4, H2, O2, NH3, at least one mineral.

11. The method according to claim 6 further comprising adjusting the microbial biomass pH to be from 7.4 up to 8.0 after separating the liquid phase.

12. An egg replacement food product wherein total weight of the egg replacement food product comprises from 76% up to 78% of water;

from 9% up to 10% of a protein microbial biomass powder comprising isolated bacterial strain deposited as VTT-E-193585 or a derivative thereof;

from 0.7% up to 1.1% of sodium chloride (NaCl);

from 9% up to 10% of an oil.

13. The egg replacement food product according to claim 12, wherein the oil is selected to be at least one of a rapeseed oil, a sunflower oil, a soy oil.

* * * * *